United States Patent [19]

Wu

[11] Patent Number: 5,387,505
[45] Date of Patent: Feb. 7, 1995

[54] PREPARATION AND ISOLATION OF SINGLE-STRANDED BIOTINYLATED NUCLEIC ACIDS BY HEAT AVIDIN-BIOTIN CLEAVAGE

[75] Inventor: Annie L. Wu, Penfield, N.Y.

[73] Assignee: Eastman Kodak Company, Rochester, N.Y.

[21] Appl. No.: 519,533

[22] Filed: May 4, 1990

[51] Int. Cl.⁶ .................. C12D 1/08; C07H 5/04; C07H 17/00
[52] U.S. Cl. ..................... 435/6; 435/91.1; 536/18.7; 536/23.1; 536/24.3
[58] Field of Search ............ 435/6, 91, 91.1; 536/63, 94, 501, 508, 518, 18.7, 23.1, 24.3

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,772,691 | 9/1988 | Herman | 536/27 |
| 4,818,680 | 4/1989 | Collins et al. | 435/6 |

FOREIGN PATENT DOCUMENTS

| | | |
|---|---|---|
| 2202328 | 3/1987 | United Kingdom. |
| 89-02931 | 4/1989 | WIPO. |
| 89-09282 | 5/1989 | WIPO. |
| 9002205 | 3/1990 | WIPO. |

OTHER PUBLICATIONS

Anderson et al., "Quatitative Filter Hybridization", in Anderson et al., Nuclei Acid Hydridization, Chap. 4, pp. 86–122. IRL Press Oxford—Washington D.C., (1987).

Syvänen, A., Med. Biolo., 64:313 (1986).
Foster et al., Nu Acid Res., 13(3):745 (1985).
Syvanen et al., Nucl. Acid Res., 14(12)5007 (1986).
*Shimkus et al., Proc. Natl. Acad. Sci. USA*, 82, pp. 2593–2597, 1985.
Kempe et al., *Nucl. Acids Res.*, 13(1), pp. 45–57 (1985).
Green, Biochem. J., 101, 774–780 (1966).
Wilchek et al., Anal. Biochem., 171:1–32 (1988).
Green, M., Advances in Protein Chem., 29:85–133 (1975).
Mullis et al., Cold Spring Symp., VLI:263–273 (1986).
Gyllensten et al., P.N.A.S., 85:7652–7656 (1988).
Green, M., in Methods in Enzymology, vol. 184, Sec. II-5 :51–68 (1990).
Stahl et al., Nucleic Acid. Res., 16(7):3025–38 (1988).
Delius et al., Nucleic Acid Res., 13(15):5457–69 (1985).
Haltman et al., Nucl. Acid. Res., 17(13):4937–46 (1989).
Richterich, P. Nucleic Acid Res., 17(6):2181–86 (1989).

*Primary Examiner*—Margaret Parr
*Assistant Examiner*—Miquel Escallon
*Attorney, Agent, or Firm*—J. Lanny Tucker

[57] ABSTRACT

A biotinylated target nucleic acid can be isolated from a mixture of nucleic acids using a capture reagent comprising avidin. The targeted nucleic acid is complexed with avidin on a substrate and separated from uncomplexed materials. The complex is heated at above about 65° C. for a suitable time to cleave the avidin-biotin bonds to release the desired targeted nucleic acid. Upon release, the targeted nucleic acid can be collected or detected in a suitable manner, such as with a complementary probe. This method is also useful for preparing single-stranded DNA for a number of uses.

21 Claims, No Drawings

PREPARATION AND ISOLATION OF SINGLE-STRANDED BIOTINYLATED NUCLEIC ACIDS BY HEAT AVIDIN-BIOTIN CLEAVAGE

FIELD OF THE INVENTION

This invention relates to methods for preparing and isolating a targeted nucleic acid which is biotinylated. These methods are useful in the fields of molecular biology, biochemistry and genetics and have industrial application in diagnostics and nucleic acid sequencing.

BACKGROUND OF THE INVENTION

Single-stranded DNA is useful in a number of important technologies. For example, the determination of the sequence of a nucleic acid has had enormous impact in the fields of molecular biology, biochemistry and genetics. Many sequencing methods require the use or generation of single-stranded DNA at some stage in the methods. Nucleic acid sequencing has promoted considerable research and commercial activity. A single nucleic acid is generally characterized by nucleotide sequence, molecular weight, size and shape. A useful sequencing procedure is described, for example, by Gyllenstein et al (*Proc.Natl.Acad.Sci.USA*, 85, p. 7652–7656, October, 1988).

Single-stranded nucleic acids are also useful as probes in medical diagnostics based on the hybridization of complementary nucleotides of nucleic acids to detect pathogens, diseases, genetic features or disease-causing situations. The DNA complex is normally stable, but the strands can be separated (or denatured) by conditions which disrupt the hydrogen bonding between complementary nucleotides.

In addition, hybridization assays are used in forensic testing, both criminal (identifying persons by samples of hair, blood or semen left at the scene of the crime or on the victim) and non-criminal (such as for paternity determinations and immigration screening).

The use of complementary nucleic acids to detect small quantities of targeted nucleic acids has been enhanced considerably by the development of polymerase chain reaction procedures as described, for example, in U.S. Pat. No. 4,683,195 (issued Jul. 28, 1987 to Mullis) and U.S. Pat. No. 4,683,202 (issued Jul. 28, 1987 to Mullis et al). Without going into detail regarding these procedures, they involve the use of a polymerase to make extension products which are complementary to the target nucleic acid strands, which extension products are denatured and multiplied themselves many times in cyclical fashion. Thus, the original targeted strands are multiplied greatly for eventual detection. In some instances, one or both primers used in such procedures are biotinylated for complexation with avidin for capture or detection.

Nucleic acids have been labeled with a number of detectable moieties in order to facilitate the detection of hybridized strands. Biotin has been commonly used as a detectable moiety because it readily combines with avidin to form stable detectable complexes.

The high affinity of biotin for the glycoprotein avidin provides the basis for many established procedures for the detection and isolation of biotin-associated proteins or nucleic acids. With the introduction of biotinylated nucleotide analogs by various researchers, it has become possible to apply this affinity system to the detection of specific nucleic acids by using biotinylated hybridization probes. The strong avidin-biotin complex can provide a single-step, high yield retrieval procedure of targeted nucleic acids from crude mixtures.

Because workers in the art have wanted to avoid harsh chemical denaturing conditions (for example, 6 molar guanidine HCl, pH 1.5) to break avidin-biotin complexes, many reagents have been synthesized to enable the captured nucleic acid to be released from the capture probe and isolated. For example, in some instances, a nucleic acid is chemically modified to have a chemically cleavable linkage between the nucleotides and the biotin. Shimkus et al (*Proc.Natl.Acad.Sci.USA*, 82, pp. 2593–2597, 1985) describe the use of a disulfide bond as a means for reversibly binding nucleotides to avidin-agarose columns. Other chemically cleavable nucleotides are described in U.S. Pat. No. 4,772,691 (issued Sep. 20, 1988 to Herman) to provide a means for chemical cleavage under relatively mild conditions.

While the chemically-modified reagents known in the art serve the desired function, it would be highly desirable to avoid the need to synthesize or purchase such reagents due to the tedious synthetic procedures and expense. It would be desirable to have a simple, but effective means for isolating or preparing biotinylated nucleic acids without harsh chemical denaturing conditions, and the need for expensive reagents.

SUMMARY OF THE INVENTION

The problems noted above are overcome with a method for isolating a biotinylated target nucleic acid from a mixture of nucleic acids, the method comprising:

A. contacting an aqueous mixture of nucleic acids, at least one of the nucleic acids being a biotinylated target nucleic acid, with a substrate having covalently attached thereto molecules of avidin or a derivative thereof, so as to form a water-insoluble complex of avidin or a derivative thereof and the at least one biotinylated target nucleic acid on the substrate, B. separating uncomplexed materials from the water-insoluble complex, C. subjecting the separated water-insoluble complex to heat above about 65° C. for a time sufficient to break substantially all of the avidin-biotin bonds in the complex to release the resulting biotinylated target nucleic acid, and D. collecting the released biotinylated target nucleic acid.

Moreover, a method for the amplification of a target nucleic acid comprises:

A. amplifying a target nucleic acid in a specimen using a polymerase chain reaction and at least one biotinylated primer to form a biotinylated target nucleic acid, B. contacting the biotinylated target nucleic acid with a substrate having covalently attached thereto molecules of avidin or a derivative thereof, so as to form a water-insoluble complex of avidin or a derivative thereof and the biotinylated target nucleic acid on the substrate, C. separating uncomplexed materials from the water-insoluble complex, D. subjecting the separated water-insoluble complex to heat above about 65° C. for a time sufficient to break substantially all of the avidin-biotin bonds in the complex to release the resulting biotinylated target nucleic acid, and E. collecting the released biotinylated target nucleic acid.

This invention also provides a method for preparing single-stranded DNA comprising:

A. amplifying a target nucleic acid in a specimen using a polymerase chain reaction and a pair of primers, only one of which is biotinylated, to form a biotinylated strand of the target nucleic acid and a nonbiotinylated strand of the target nucleic acid in admixture, B. contacting the mixture with a substrate having covalently attached thereto molecules of avidin or a derivative thereof,
so as to form a water-insoluble complex of avidin or a derivative thereof and the biotinylated strand of the target nucleic acid on the substrate, C. separating the nonbiotinylated strand from the water-insoluble complex by washing, D. subjecting the separated water-insoluble complex to heat above about 65° C. for a time sufficient to break substantially all of the avidin-biotin bonds in the complex to release the biotinylated strand of the target nucleic acid, and E. collecting the released biotinylated strand of the target nucleic acid.

The present invention provides a simple and relatively inexpensive method for capturing, isolating or preparing biotinylated nucleic acids. It avoids the harsh chemical denaturing conditions that are described in the literature, and yet the need for preparing or purchasing expensive biotinylated reagents is also avoided. These advantages are possible by cleaving avidin-biotin complexes by heating the complex to a temperature greater than 65° C. for a time sufficient to break the complex. In doing so, however, the attached nucleic acids are not harmed (assuming that unnecessarily high temperatures are not used). Generally, temperatures in the range of 85°–100° C. for a few seconds to a few minutes are sufficient. More details of the procedure are given below.

DETAILED DESCRIPTION OF THE INVENTION

The present invention is directed to the preparation, amplification or isolation of biotinylated nucleic acids, particularly those predetermined (that is, target) nucleic acids in a mixture of nucleic acids. Such materials can be found in cellular or vital samples, hair, body fluids or tissues of humans or animals containing genetic DNA or RNA which can be biotinylated and detected.

Some of the uses of biotinylated nucleic acids isolated with this invention include diagnostic methods, nucleic acid sequencing and forensic testing. The invention can also be used to obtained large quantities of a specific nucleic acid from a mixture of nucleic acids resulting from a chemical synthesis. Other uses of purified biotinylated nucleic acids are readily apparent to one skilled in the art.

Nucleic acids can be obtained from various sources including plasmids, naturally occurring DNA or RNA from any source (bacteria, yeast, viruses, plants, higher animals and humans). They may be extracted from various tissues and fluids using materials and procedures known in the art.

In a preferred embodiment, the biotinylated target nucleic acid is isolated from a mixture of nucleic acids after amplification using polymerase chain reaction, which is described in more detail below.

Biotinylated nucleic acids are isolated from an aqueous mixture of nucleic acids by contacting the mixture with a substrate having avidin molecules covalently attached thereto. This contact can be accomplished in any suitable fashion, such as by mixing the substrate in particulate form within the aqueous mixture, or by applying the mixture to the substrate which is in the form of a film. The method of contact will depend largely on the type of substrate used, of which there are many, including films, porous filters or matrices, beads, tubes, microtiter plates and others known in the art. Contact can occur at any suitable temperature, although it is usually at room temperature, and will occur for at least 10 seconds and up to 5 hours in order to allow sufficient complexation of biotin and avidin on the substrate.

"Biotin" as a term is used herein to include hexahydro-2-oxo-1H-thieno[3,4]imidazole-4-pentanoic acid (also known as Vitamin H) and biotin derivatives such as biotin-ε-N-lysine, biocytin hydrazide, amino or sulfhydryl derivatives of 2-iminobiotin and biotinyl-ε-aminocaproic acid-N-hydroxysuccinimide ester, sulfosuccinimideiminobiotin, biotinbromoacetylhydrazide, p-diazobenzoyl biocytin and 3-(N-maleimidopropionyl)biocytin as lone as these derivatives can be suitable attached to nucleic acids.

Biotinylated nucleic acids are readily prepared using procedures known in the art. For example, a preferred procedure is described in detail in WO-A-89/02931, incorporated herein by reference. This procedure is generally as follows: A phthalimido triethyleneglycol phosphoramidite is incorporated at the 5'-end of the oligonucleotide of interest, and the phthalimide is converted to a primary amino group by hydrolysis using ammonium hydroxide. N-hydroxysuccinimidobiotin is then attached to the free amino group to form the desired biotinylated nucleic acid.

As used herein, the term "avidin" refers to the protein commonly found in egg whites as well as derivatives or equivalents thereof, such as streptavidin, succinylated avidin, monomeric avidin or an antibody to biotin. Avidin can be covalently attached to a suitable support through reactive groups on the substrate surface. There are many useful reactive groups which react with a free amine group of the avidin molecule. Such groups include, but are not limited to, carboxy, active halogen, activated 2-substituted ethylsulfonyl, activated 2-substituted ethylcarbonyl, active ester, vinylsulfonyl, vinylcarbonyl, aldehyde, epoxy, amino and sulfhydryl. Particularly useful reactive groups are carboxy, active halogen, activated 2-substituted ethylsulfonyl and vinylsulfonyl, all of which are known in the art. Some of these groups will react directly with the avidin molecule while others, such as carboxy, require the use of a compound to produce an intermediate which will react with the avidin molecule. Preparation of substrates, such as films and particles having these reactive groups is well known in the art. In particular, small polymeric particles which are preferred are readily prepared using emulsion or suspension polymerization techniques. The following references provide useful details for preparing some of such substrates and reacting avidin thereto: U.S. Pat. No. 4,582,810 (issued Apr. 15, 1986 to Rosenstein), WO-A-84/03358 (published Aug. 30, 1984), EP-A-0 302 715 (published Feb. 8, 1989, U.S. Ser. No. 373,304 (filed Jun. 29, 1989 by Sutton et al) and U.S. Ser. No. 273,779 (filed Nov. 21, 1988 by Burdick et al), all of which are incorporated herein by reference.

A particularly useful substrate is a polymeric particle composed of a polymer, at least one its outer surface, prepared from one or more ethylenically unsaturated polymerizable monomers having carboxy, active halogen atom, activated 2-ethylsulfonyl or vinylsulfonyl groups for reaction with avidin.

Useful polymeric particles generally have an average diameter of at least about 0.01 $\mu$meter, with diameters in the range of from about 0.1 to about 5 $\mu$meters being preferred. The particles can be composed of the same polymer throughout, or they can be core-shell polymers as described, for example, in U.S. Pat. No. 4,703,018 (issued Oct. 27, 1987 to Craig et al) and EP-A-0 280 556 (published Aug. 31, 1988) where the shell polymer has the requisite reactive groups.

Once the avidin-biotin complex has been formed, thereby immobilizing the biotinylated nucleic acid, uncomplexed materials are separated from the complex using a suitable procedure such as centrifugation, filtration, washing and other techniques known in the art. Various wash steps and fluids are also known in the art including wash solutions containing salts, chaotropic agents, N,N-dimethylformamide or dimethylsulfoxide. Preferably, separation is carried out using a microporous filtration membrane such as those marketed by Pall Corp. as BIODYNE TM, LOPRODYNE TM or ULTIPORE TM microporous membranes. The membranes can be mounted in filter or test devices for convenience and analytical determination, such as the disposable test devices commercially available as the SURECELL TM test kits marketed by Eastman Kodak Company.

The immobilized complex is then subjected to heat for a sufficient time and at a sufficient temperature to break the avidin-biotin bond, releasing the biotinylated nucleic acid of interest. The time and temperature will vary inversely. The higher the temperature, the less time will be needed to break the bond. Generally, a temperature about 65° C. is minimum for breaking the bond in a reasonable time (about 30 minutes). Preferably, the process is simplified even more by heating the complex above about 90° C. for at least 5 minutes, and more preferably, by heating for about 5 to about 30 minutes above about 95° C. Although temperatures over 100° C. can be used, it is usually not practical and little efficiency is to be gained by the higher temperatures. The upper temperature where the nucleic acids are damaged is considerably higher (about 300° C.). Routine experimentation can be carried out to find the optimum time and temperature for releasing the biotinylated nucleic acid.

The released biotinylated target can then be collected or further manipulated in various research or diagnostic procedures. It can be collected, for example, using a capture probe having a complementary oligonucleotide. More generally, the released biotinylated nucleic acid is used for diagnostic purposes to detect infectious diseases or cancerous cells.

It should be understood that the biotinylated nucleic acid can be a single-stranded or double-stranded molecule. If it is a double-stranded molecule, one or both of the strands are biotinylated.

The present invention can also be used to amplify a target nucleic acid using polymerase chain reaction and a biotinylated primer, and isolating the amplified biotinylated target nucleic acid using the separation, heating and collection steps described above.

More particularly, a target nucleic acid is a specimen (such as a biological fluid) is amplified using polymerase chain reaction as described in detail, for example, in U.S. Pat. Nos. 4,683,195 and 4,683,202 (both noted above), both incorporated herein by reference. Example 1 below illustrates a representative polymerase chain reaction amplification procedure.

As used herein in referring to primers, the term "oligonucleotide" refers to a molecule comprised of two or more deoxyribonucleotides or ribonucleotides, and preferably more than three. The exact size is not critical (except for the probe described below) but depends upon many factors including the ultimate use or function of the oligonucleotide. The oligonucleotide may be derived synthetically or by other methods known in the art.

The term "primer" refers to an oligonucleotide, whether naturally occurring or synthetically produced, which is capable of acting as a point of initiation of synthesis when placed under conditions in which synthesis of a primer extension product complementary to a nucleic acid strand is induced. Such conditions include the presence of nucleotides (such as the four standard deoxyribonucleoside triphosphates) and an agent for polymerization such as a DNA polymerase, and suitable temperature and pH.

A mixture of primers can be used in the amplification, and a set of primers is generally used for each nucleic acid sequence to be amplified. Each primer is substantially complementary to a nucleic acid sequence of the target DNA. By "substantially complementary" is meant that there are a sufficient number of bases on the primer that match with the corresponding bases in the target DNA that the primer will hybridize with that sequence. It does not mean, however, that every base pair will match.

The primers are generally single-stranded. The exact size of each primer will vary depending upon the use contemplated, the complexity of the target sequence, reaction temperature and the source of the primer. Generally, the primers used in this invention will have from 15 to 50 nucleotides, and preferably, they have from 20 to 30 nucleotides.

Primers useful herein can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use. Naturally occurring primers isolated from biological sources are also useful (such as restriction endonuclease digests).

At least one of the primers used in the method is biotinylated, that is, it has a biotin moiety covalently attached thereto. Such conjugates of primer and biotin can be readily prepared using known technology, described for example in by Connolly in *Nuclei Acids Research*, 15(7), 3131 (1987). A preferred procedure for biotinylating a primer is described in WO-A-89/02931 (noted above).

The denatured strands of a target nucleic acid are contacted with suitable primers under conditions such that a mixture of hybridized products of primers and target DNA strands are formed. Such conditions are those normally used for amplification as described in U.S. Pat. No. 4,683,202 (noted above). Primer extension products are then formed with at least one of the hybridized products followed by additional priming and extension product formation. After denaturation (that is, separation of complementary products), the replicated biotinylated nucleic acid is now the target of interest and can be isolated using the avidin-biotin reaction, heating and collection steps described above.

The present invention is also useful for amplification of a specific nucleic acid having two complementary strands. Most nucleic acid sequences of interest already are double-stranded, such as those found in DNA. However, single-strand nucleic acid sequences, such as mRNA, can be similarly detected after it is converted to a double-stranded sequence using reverse transcriptase.

A specific nucleic acid sequence is reproduced using the nucleic acid containing that sequence as a template. If the nucleic acid contains two strands, it is necessary to separate the strands, either as a separate step or simultaneously with the formation of primer extension products. Denaturing can be accomplished using any suitable physical, chemical or enzymatic means as described in the art. Heating to a suitable temperature is a preferred means.

Once the separated strands are available for use, synthesis of additional nucleic acid strands can be carried out using the primers in a buffered aqueous solution generally at a pH of from about 7 to about 9. Preferably, a molar excess of the primers is added to the buffered solution, and specific amounts are taught in the art (for example, U.S. Pat. No. 4,683,202, noted above). The deoxyribonucleoside triphosphates dATP, dCTP, dGTP and dTTP are also added to the synthesis mixture in adequate amounts and the resulting solution is heated to about 90°-100° C. for up to 10 minutes, and preferably from about 1 to about 4 minutes. After this heating, the solution is preferably cooled to room temperature, and an appropriate agent for inducing (or catalyzing) the formation of primer extension products is introduced. This inducing agent is generally known in the art as a polymerization agent. Reaction to form these products is carried out under known conditions (generally from room temperature to that temperature at which polymerization no longer occurs).

The polymerization agent may be any compound, or combination of reagents, which will function to accomplish the synthesis of primer extension products, including enzymes (for example, *E. coli* DNA polymerase I, T4 DNA polymerase, Klenow polymerase, reverse transcriptase and others known in the art). Particularly useful enzymes are thermally stable enzymes, cloned or naturally occurring, such as those obtained from various Thermus bacterial species. Other polymerization agents are described in U.S. Pat. No. 4,683,202 (noted above).

Preferred thermally stable enzymes are DNA polymerases from *Thermus aquaticus* as described in EP-A-0 258 017 (published Mar. 2, 1988) and WO-A-89/06691 (published Jul. 27, 1989). Useful polymerases can also be obtained from strains of *Thermus thermophilus* (such as strain HB-8), as described for example by Ruttimann et al, *Eur. J. Biochem.*, 149, pp. 41–46 (1985), Hudson et al, *J. Gen. Microbiol.*, 132, pp. 531–540 (1986) and Costa et al, *Proc. Fed. Eur. Microbiol. Soc. Symp.*, pp. 82–97 (1988). Still other useful enzymes are described by Rossi et al, *Syst. Appl. Microbiol.* 7(2–3), pp. 337–341, 1986. Some useful polymerases are commercially available. Generally, the synthesis of extension products will be initiated at the 3' end of each primer and proceed in the 5' to 3' direction along the template until synthesis is terminated. Some polymerization agents (for example, reverse transcriptase) may proceed in the 3' to 5' direction along the template.

The newly formed primer extension products comprising the newly synthesized strands and their respective primers form double-stranded molecules with the initial target strands which are used in the succeeding steps of the method. These strands are then separated by denaturation as described above to provide single-stranded molecules, onto which new nucleic acids are synthesized as described above. Additional reagents may be needed to keep the amplification procedure going, after which most of the extension products will consist of the specific nucleic acid sequence bounded by the primers (that is, complementary products).

The steps of strand separation and extension product synthesis can be repeated as often as needed to produce the desired quantity of the specific nucleic acid needed for the use, for example detection. Generally, the sequence of steps is repeated at least once, and preferably at least 10 to 50 times.

In a preferred embodiment, a method for preparing single-stranded DNA comprises:

A. amplifying a target nucleic acid in a specimen using a polymerase chain reaction and a pair of primers, only one of which is biotinylated, to form a biotinylated strand of the target nucleic acid and a nonbiotinylated strand of the target nucleic acid in admixture, B. contacting the mixture with a substrate having covalently attached thereto molecules of avidin or a derivative thereof, so as to form a water-insoluble complex of avidin or a derivative thereof and the biotinylated strand of the target nucleic acid on the substrate, C. separating the nonbiotinylated strand from the water-insoluble complex by washing, D. subjecting the separated water-insoluble complex to heat above about 65° C. for a time sufficient to break substantially all of the avidin-biotin bonds in the complex to release the biotinylated strand of the target nucleic acid, and E. collecting the released biotinylated strand of the target nucleic acid.

The target nucleic acid can be obtained from any source, including plants, microorganisms, animals, humans, as noted above. It is particularly desirable to amplify a Human Leukocyte Antigen (HLA) DNA or DNA associated with retroviruses, such as HIV-I. Those skilled in the art would be able to amplify other single-stranded or double-stranded nucleic acids with the present invention.

The following examples are presented to illustrate the invention. The scope of the invention is not to be so limited. All percentages are based on weight unless otherwise noted.

EXAMPLE 1

Amplification and Isolation of Biotinylated HLA DNA

This example demonstrates the use of the present invention to amplify a target HLA DNA using a biotinylated primer, and isolation of the amplified nucleic acid using avidin-biotin complexation and denaturation.

Materials

A reagent composed of polymeric particles of poly[styrene-co-m & p-(2-chloroethylsulfonylmethyl)styrene] (95.5:4.5 molar ratio) was used to immobilize the amplified nucleic acid. Avidin was covalently attached to these particles to form the reagent as follows:

Egg white avidin (SIGMA TM Chemical Co., 6 ml of a solution containing 6 mg avidin dissolved in 6 ml of deionized distilled water) was added to a solution of borate buffer (50 ml of a 0.05 molar solution, pH 8.5) containing 0.01% merthiolate in a polypropylene centrifuge tube. This tube was then capped and shaken vigorously. The dispersion of polymeric particles (1.35 ml, 15.5% solids, average particle diameter of 2.54 μm) was added to the tube, it was capped again and rotated end-over-end for 24 hours. The resulting dispersion was washed with glycine buffer (0.1 molar, pH 8.5) containing merthiolate (0.01%), and resuspended in fresh glycine buffer to product a stock solution containing the desired reagent (0.3% solids).

A DNA polymerase was used in amplification which was isolated from *Thermus aquaticus* and had an activity of about 4 I.U./μl.

HLA homozygous cell line FPF (from Human Genetic Mutant Cell Deposit at Camden, N. J.) was the source of DNA from the HLA-DQα locus ($10^6$ copies).

The primers used in the amplification procedure had the following nucleic acid sequences:
   Primer 1: 5'-Y-CTCGGATCCGCATGTG-CTACTTCACCAACG-3'
   Primer 2: 5'-GGTCCCCTCCAG-GACTTCCTTCTGGCT-3'
wherein Y represents a biotintetraethylene glycol linker arm prepared and attached using the procedure described in WO-89/02931 (noted above).

The dNTPs used in the polymerase chain reaction were labeled with tritium.

A salt wash solution included sodium chloride (17.6 g), sodium phosphate (17 mmolar), ethylenediaminetetraacetic acid (2 mmolar), sodium dodecyl sulfate (0.5%) in 1 liter of water (pH 7.4).

Method

Two samples of the target nucleic acid were added to a buffered solution (100 μl) containing tris(hydroxymethyl)aminomethane hydrochloride (67 mmolar, pH 8.8), ammonium sulfate (16.6 mmolar), magnesium chloride (2.5 mmolar) and gelatin (10 μg). The primers described above were added (20 pmoles of each), followed by addition of the tritiated dNTPs (0.175 mmolar of each), the DNA polymerase identified above (12 units) and the DNA segments noted above. Amplification was carried out for 35 consecutive cycles as follows:

| | | |
|---|---|---|
| 70° C. | rising to 95° C. | 1 minute |
| 95° C. | | 0.5 minute (denature) |
| 95° C. | lowering to 65° C. | 1.25 minutes |
| 65° C. | | 0.5 minute (hybridize) |
| 65° C. | rising to 70° C. | 0.75 minute |
| 70° C. | | 1 minute (extend primers) |

The resulting mixtures of nucleic acids were each filtered to remove unextended biotinylated primers and excess tritiated dNTPs. The resulting mixtures (100 μl) were mixed with the polymeric particles having avidin attached thereto (2 mg) each to a final volume of 200 μl, and incubated at 37° C. for one hour to form the avidin-biotin complex.

After washing one of the mixtures three times with the salt solution identified above at 25° C., the amount of tritium label was determined. The results indicated that both complementary target nucleic acid strands were immobilized on the particles.

The second mixture was washed three times with sodium hydroxide (0.1 normal) to denature the immobilized double-stranded nucleic acids. After centrifugation to remove the water-soluble materials, the amount of tritium label in the water-insoluble residue was measured and found to be about 50% of the total count, indicating that the strands on the particles were successfully denatured.

The single-stranded nucleic acid on the particles was then isolated by heating a suspension of the immobilized material (in the salt solution noted above, total volume of 100 μl) at 95° C. for 30 minutes to break the avidin-biotin bonds. The particles having avidin attached thereto were removed by centrifugation, and the supernatant containing the HLA nucleic acid of interest was collected. Measurement of the tritium in the supernatant revealed a full recovery of the single-stranded nucleic acid.

EXAMPLE 2

Detection of Target HLA DNA Using Color Detection

This example demonstrates the practice of this invention to detect HLA DNA using a dye-providing detection composition.

Materials

The reagents described in Example 1 above were used, except that the dNTP's were not tritiated. The following additional reagents were also used: A probe prepared from an oligonucleotide complementary to the target nucleic acid having the following sequence:

5'-X-AGTACTCGGCATCAGGC-3' wherein X represents an aminotetraethylene glycol linker having 16 ethylene glycol units, prepared and attached to the oligonucleotide according to the procedures of WO-A-89/02831 (noted above).

The oligonucleotide was covalently attached to particles of poly(styrene-co-acrylic acid) (70:30 molar ratio) having an average diameter of 2.1 μm, to form a probe as follows:

An aqueous solution of the particles (1 ml, 30 mg particles) was centrifuged and the supernatant removed. The particles were then resuspended in glass-distilled water (1 ml) by vigorous vortexing. The suspension was again centrifuged, the supernatant removed and the particles resuspended in a solution (1 ml) of methylimidazole (0.2 molar) and sodium chloride (3 normal, pH 7).

To this suspension was added the noted modified oligonucleotide (2.5 nmoles) and the resulting mixture was mixed well. The activating compound 1-(3-dimethylaminopropyl)-3-ethylcarbodiimide hydrochloride (5 mg) was added, and after thorough mixing by vortex, the reaction mixture was incubated at room temperature with occasional mixing for at least two hours (generally about 15 hours).

The supernatant was first removed after centrifugation, and the solids were washed with the following fluids by centrifugation and pipetting off the supernatant between solutions: a) three times with glass-distilled water (1 ml), and b) three times with a buffer solution (1 ml) of sodium chloride (0.018 molar), sodium phosphate (1 mmolar), ethylenediaminetetraacetic acid (0.1 mmolar) and dodecyl sulfate (0.5%, pH 7.4). The buffer solution had been prewarmed to 70° C.

The last wash, the solids were resuspended in glass-distilled water to a final volume of 1 ml to make a 3% particle dispersion which was stored at 4° C. until use.

A conjugate of horseradish peroxidase and avidin was obtained from a commercially available SEE-QUENCE ™ HLA-D kit (Eastman Kodak Co.).

A leuco dye composition for providing a detectable dye was prepared as follows: solid 2-(4-hydroxy-3,5-dimethoxyphenyl)-4,5-bis(4-methoxyphenyl)imidazole leuco dye (to make a 0.1% solution) was dissolved in a solution of poly(vinyl pyrrolidone) (20%) in sodium phosphate buffer (5 mmolar). This solution was then added to a solution containing hydrogen peroxide (10 mmolar), 4'-hydroxy-acetanilide (5 mmolar) and diethylenetriaminepentaacetic acid (10 mmol) in sodium phosphate buffer to produce a final concentration of 1% polymer and 0.005% leuco dye.

Assay

The target nucleic acid was amplified and reacted with the avidin-polymer reagent to form the avidin-biotin complex as described in Example 1 above.

The mixture was then washed three times with sodium hydroxide (0.1 normal) to denature the immobilized double-stranded nucleic acid. After centrifugation to remove soluble materials, the single-stranded nucleic acid was isolated by heating as suspension of the immobilized nucleic acid (in the salt solution noted above, 100 $\mu$l total volume) at 95° C. for 30 minutes to break the avidin-biotin bond. The particles having avidin attached thereto were removed by centrifugation. The supernatant contained the single-stranded HLA nucleic acid of interest.

The isolated nucleic acid solution (10 $\mu$l) was mixed with the probe (200 $\mu$g) in a solution comprising sodium phosphate (0.125 molar), sodium chloride (2.5 normal) and ethylenediaminetetraacetic acid (5 mmolar) having a pH of 6.8. The final volume was 30 $\mu$l. This solution was incubated for 10 minutes at 38° C. to hydribize the probe with the isolated single-stranded nucleic acid.

The solution was added to the test wells of a SURE-CELL ™ disposable test device (Eastman Kodak Co.) containing LOPRODYNE ™ microporous filtration membranes (Pall Corp.) in the bottoms of the test wells, and the fluid was allowed to drain through the membranes immediately. The hybridized product of the probe and target nucleic acid was retained on the surface of the membranes. The product was washed with a solution (300 $\mu$l) comprising sodium phosphate (0.85 mmolar), sodium chloride (15 mmolar) and sodium dodecyl sulfate (0.5%), which had been prewarmed to 55° C. The peroxidase-avidin reagent (30 $\mu$l containing 2.3 ng of reagent) was added, and the SURECELL ™ test device was incubated at room temperature for two minutes. The excess peroxidase-avidin reagent was washed through the filter with a solution (200 $\mu$l) of tris(hydroxymethyl)aminomethane (50 mmolar), sodium dodecyl sulfate (2.4%), sodium chloride (0.5 normal) and 1-methyl-2-pyrrolidinone (10%, pH 8.8). The leuco dye composition (50 $\mu$l) was then added to the test wells, and the appearance of a red dye on the membranes in five minutes indicated the presence of the target HLA nucleic acid.

The invention has been described in detail with particular reference to preferred embodiments thereof, but it will be understood that variations and modifications can be effected within the spirit and scope of the invention.

I claim:

1. A method for the amplification of a target nucleic acid, said method comprising:
   A. amplifying a target nucleic acid in a specimen using a polymerase chain reaction and at least one biotinylated primer to form a biotinylated target nucleic acid,
   B. contacting said biotinylated target nucleic acid with a substrate having covalently attached thereto molecules of avidin or a derivative thereof,
      so as to form a water-insoluble complex of avidin or a derivative thereof and said biotinylated target nucleic acid on said substrate,
   C. separating uncomplexed materials from said water-insoluble complex,
   D. breaking the avidin-biotin bonds in said water-insoluble complex to release the resulting biotinylated target nucleic acid,
      said breaking consisting essentially of heating said water-insoluble complex to above about 65° C. for at least 5 minutes, and
   E. collecting said released biotinylated target nucleic acid.

2. The method of claim 1 wherein said water-insoluble complex is heated at above about 90° C.

3. The method of claim 2 wherein said water-insoluble complex is heated at above about 95° C. for from about 5 to about 30 minutes.

4. The method of claim 1 wherein said substrate is a polymeric particle.

5. The method of claim 4 wherein said polymeric particle is composed of a polymer prepared from one or more ethylenically unsaturated polymerizable monomers having groups covalently reactive with avidin or a derivative thereof, said reactive groups selected from the group consisting of carboxy, an active halogen atom, activated 2-ethylsulfonyl and vinylsulfonyl.

6. The method of claim 1 wherein a single biotinylated primer is used in said amplification.

7. The method of claim 1 wherein said polymerase chain reaction is carried out using a thermally stable DNA polymerase.

8. The method of claim 1 for the amplification of a target nucleic acid which is HLA DNA.

9. The method of claims 1 wherein said released target biotinylated nucleic acid is collected by centrifugation.

10. A method for preparing single-stranded DNA comprising:
   A. amplifying a target nucleic acid in a specimen using a polymerase chain reaction and a pair of primers, only one of which is biotinylated, to form a biotinylated strand of said target nucleic acid and a nonbiotinylated strand of said target nucleic acid in admixture,
   B. contacting said mixture with a substrate having covalently attached thereto molecules of avidin or a derivative thereof,
      so as to form a water-insoluble complex of avidin or a derivative thereof and said biotinylated strand of said target nucleic acid on said substrate,
   C. separating said nonbiotinylated strand from said water-insoluble complex by washing,
   D. breaking the avidin-biotin bonds in said water-insoluble complex to release the biotinylated strand of said target nucleic acid, said breaking consisting essentially of heating said water-insoluble complex to above about 65° C. for at least 5 minutes, and E. collecting said released biotinylated strand of said target nucleic acid.

11. The method of claim 10 for preparing single-stranded HLA DNA.

12. The method of claim 10 for preparing single-stranded HIV-I DNA.

13. The method of claim 10 wherein said water-insoluble complex is heated at above about 90° C. for at least 5 minutes.

14. The method of claim 13 wherein said water-insoluble complex is heated at above about 95° C. for from about 5 to about 30 minutes.

15. The method of claim 10 wherein said substrate is a polymeric particle.

16. The method of claim 10 wherein said released biotinylated strand is detecting using an oligonucleotide probe substantially complementary thereto.

17. A method for the determination of a target nucleic acid, said method comprising A. amplifying a target nucleic acid in a specimen using a polymerase chain reaction and at least one biotinylated primer, to form a biotinylated target nucleic acid, B. contacting said biotinylated target nucleic acid with a substrate having covalently attached thereto molecules of avidin or a derivative thereof, so as to form a water-insoluble complex of avidin or a derivative thereof and said biotinylated target nucleic acid on said substrate, C. separating uncomplexed materials from said water-insoluble complex, D. breaking the avidin-biotin bonds in said water-insoluble complex to release the resulting biotinylated strand of said target nucleic acid, said breaking consisting essentially of heating said water-insoluble complex to above about 65° C. for at least 5 minutes, E. contacting said released biotinylated target nucleic acid with at least one oligonucleotide probe complementary to said biotinylated strand to form a water-insoluble hybrid product, F. separating nonhybridized, water-soluble materials from said water-insoluble hybrid product, G. contacting said water-soluble hybrid product with an enzyme-avidin conjugate to form a water-insoluble complex between said conjugate and said hybrid product, and H. detecting said water-insoluble complex as a measure of the amount of target nucleic acid in said specimen.

18. The method of claim 17 wherein said separation step F is carried out using a microporous filtration membrane.

19. The method of claim 17 wherein said complex contains peroxidase and complex detection is accomplished by contacting it with a dye-providing composition which provides a dye in the presence of peroxidase and hydrogen peroxidase.

20. The method of claim 19 wherein said dye-providing composition comprises a triarylimidazole leuco dye.

21. The method of claim 17 wherein said oligonucleotide probe comprises a polymeric particle to which is attached an oligonucleotides having the sequence:

5'-AGTACTCGGCATCAGGC-3'.

* * * * *